United States Patent [19]

Maruschak

[11] Patent Number: 5,601,894
[45] Date of Patent: Feb. 11, 1997

[54] INSULATED INTRAVENOUS ADMINISTRATION TUBING AND DRIP CHAMBERS

[75] Inventor: Gary F. Maruschak, Baltimore City, Md.

[73] Assignee: Johns Hopkins Hospital, Baltimore, Md.

[21] Appl. No.: 499,091

[22] Filed: Jul. 6, 1995

[51] Int. Cl.⁶ ........................................ B32B 7/00
[52] U.S. Cl. ...................... 428/35.9; 428/920; 428/35.2; 428/35.7; 138/110; 138/118.1; 138/149; 604/113
[58] Field of Search .................... 428/35.7, 36.91, 428/36.9, 920, 35.2, 35.4, 36.6; 138/110, 113, 118.1, 148, 149; 604/113, 264, 280

[56] References Cited

U.S. PATENT DOCUMENTS

| | | | |
|---|---|---|---|
| 3,612,059 | 10/1971 | Ersek | 604/113 |
| 4,014,369 | 3/1977 | Kobres | 138/113 |
| 4,106,488 | 8/1978 | Gordon | 424/1 |
| 4,359,453 | 11/1982 | Gordon | 424/1 |
| 4,645,489 | 2/1987 | Krumme | 604/65 |
| 4,731,505 | 3/1988 | Crenshaw et al. | 138/110 |
| 4,804,367 | 2/1989 | Smith | 604/113 |
| 4,906,496 | 3/1990 | Hosono et al. | 138/113 |
| 4,908,012 | 3/1990 | Moise | 604/151 |
| 4,934,336 | 6/1990 | White | 604/113 |
| 4,972,759 | 11/1990 | Nelson | 138/149 |
| 5,056,526 | 10/1991 | Khalil | 128/692 |
| 5,149,321 | 9/1992 | Klatz | 604/52 |
| 5,211,631 | 5/1993 | Sheaff | 604/113 |
| 5,260,020 | 11/1993 | Wilk | 604/21 |
| 5,279,598 | 1/1994 | Sheaff | 604/290 |

Primary Examiner—Ellis Robinson
Assistant Examiner—Christos S. Kyriakou
Attorney, Agent, or Firm—Cushman Darby & Cushman IP Group of Pillsbury Madison & Sutro LLP

[57] ABSTRACT

A device or apparatus to insulate intravenous administration tubing is disclosed. The insulation device consists of a long tubular-like structure which consists of two concentric channels, an inner channel and an outer channel. The inner channel accepts and encloses the actual tubing in which warm fluid flows. Three key functions are achieved with this device. One key function of the insulation device is to maintain the inner channel centered within the outer channel; this provides for maximum insulation efficiency/properties with the minimum of separating space. Another equally key function is to provide for transparency; the more transparent the insulation device the better the ability of the user to see the quality of the warm fluid flowing within, i.e. detect air bubbles. Another key function is to provide for ease of set-up and reusability. All components are to be made of clear, flexible, light-weight materials to permit insulation and visualization of I.V. fluids and air bubbles. The insulation device has particular use, but not limited to, in preventing convective heat loss of warmed I.V. fluid as it flows through the inserted patient I.V. tubing, that would otherwise be exposed to ambient room temperature.

17 Claims, 6 Drawing Sheets

FIG. 5

INSULATED INTRAVENOUS ADMINISTRATION TUBING AND DRIP CHAMBERS

This invention relates to method and apparatus for insulating warmed intravenous fluid from ambient temperature losses to minimize and prevent a significant decrease in warmed I.V. fluid temperature as the I.V. fluid passes through the I.V. administration set and tubing to a patient.

BACKGROUND OF THE INVENTION

Sterile fluids for intravenous (I.V.) administration into the human body often require warming from ambient temperature (20° C.) to approximate body temperature (37° C.) before or during their introduction. The purpose of warming I.V. fluids and chilled blood to approximately 37° C. is to improve the maintenance of body temperature. This is especially true during anesthesia and surgery when body temperature falls due to surgical exposure of large body surface areas to ambient temperature and interference of normal body thermo-regulatory mechanisms by anesthesia. This results in the patient becoming cool, often shivering post-operatively; patients may stay longer in the recovery room to recover from hypothermia.

Current technology to provide warm I.V. fluids to patients undergoing anesthesia and surgery are in-line fluid warmers and external fluid warmers. In-line fluid warmers heat I.V. fluid up to body temperature by applying heat directly (via an in-line heating element) to the I.V. fluid as it passes from the I.V. fluid reservoir (glass bottle or plastic bag) at ambient temperature to the patient. The in-line heating elements for in-line I.V. fluid warmers are disposable and costly per patient use. The disposable cost increases as the maximum flow rate of maintained heated 37° C. I.V. fluid to the patient increases.

External I.V. fluid warmers heat the I.V. fluid (in bulk) to 37° C. before administration to the patient. The external I.V. fluid heaters heat 6 to 20 separate I.V. fluid containers (plastic bags or glass bottles) simultaneously to approximately body temperature. The warmed I.V. bags are removed from the external heater as needed and placed into use, generally by hanging them from an I.V. pole and connecting to an administration set (which usually consist of drip chamber, I.V. tubing, roller clamps & connectors) and finally attaching to the patient's I.V. cannula. After hanging, the warmed I.V. fluid bags cool down toward ambient temperature as time goes by, and further lose temperature as the warmed I.V. fluid passes through the un-heated I.V. administration set at ambient temperature. Slower I.V. fluid flow rates result in cooler delivered I.V. fluids to the patient because the I.V. fluid simply cools down with time while passing through the interconnecting tubing of the administration set, exposed to ambient temperature, before it actually enters the patient. This cooling effect with low I.V. fluid flow rates also affects in-line fluid warmers during passage through the I.V. tubing from in-line warming device to patient. Conversely, I.V. fluid flow rates greater than 100 ml/minute (in external fluid warmers) deliver warmer fluid to the patient, up to bag or reservoir temperature near 37° C.

Advantages exist in preventing heat loss of pre-warmed I.V. fluids during flow through I.V. administration tubing from I.V. reservoir bag or bottle to the patient's anatomic administration site. The use of pre-warmed I.V. fluids can be promoted as a practical, less expensive and more efficient method of administering warm I.V. fluids to patients as opposed to in-line I.V. fluid warmers. Compared to in-line I.V. fluid warmers, pre-warmed I.V. fluids are: 1) less expensive, 2) less complicated to set up and administer, and 3) less bulky because it does not require an active heating source to be placed near the patient.

It is an object of this invention to provide a flexible and transparent insulation device to be attached to I.V. tubing from I.V. reservoir bag or bottle to the patient anatomic administration site.

It is a further object of this invention to use a clear, light-weight insulation material to provide less bulk near the patient and ability to visualize air bubbles in the patient I.V. tubing.

It is a yet a further object of this invention to provide a simple means to attach or insert the patient I.V. tubing into the device.

Other objects and advantages will become apparent in light of the attached drawings and description of the invention presented hereinbelow and the appended claims.

SUMMARY OF THE INVENTION

In accordance with the present invention, there is disclosed equipment which is useful to insulate I.V. administration tubing used therewith. A purpose of the invention is to permit easy placement of the patient's I.V. administration tubing within two flexible, visually-clear or transparent, tube-like, concentric channels separated by an insulating space.

The invention tubing includes an outer channel that forms an outer covering of the device. The outer channel is separated from an inner channel by an insulating space. The outer channel also provides a split or separation aligned with and attached to the inner channel by means of central support structures. The attachment of the inner and outer channel separations by means of the central support structures provides centering and forms an access slit or separation through which the patient's I.V. tubing can be inserted. The central support structures center and maintain the inner channel within the outer channel.

Additional ancillary centering support structures may be required to keep the inner channel centered and maintained within the outer channel when the course of the patient's I.V. tubing: 1) acutely bends 2) lays against other surfaces, or 3) is physically pressed against or placed upon by other devices or structures in the immediate environment.

The clear flexible, tubing of the invention can be closed or sealed with a tape-like means or capping material at each end to prevent air movement and heat loss by convection.

Once the patient's I.V. tubing is inserted into the snap-on insulation tubing or device, the I.V. tubing can be secured within the insulation device by tape, velcro closures, or other fastening means to keep the access split or separation closed.

BRIEF DESCRIPTION OF THE DRAWINGS

For a more complete understanding of the invention reference should be made to the drawings wherein.

DESCRIPTION OF PREFERRED EMBODIMENTS

Figures 1A, 1B, 1C:
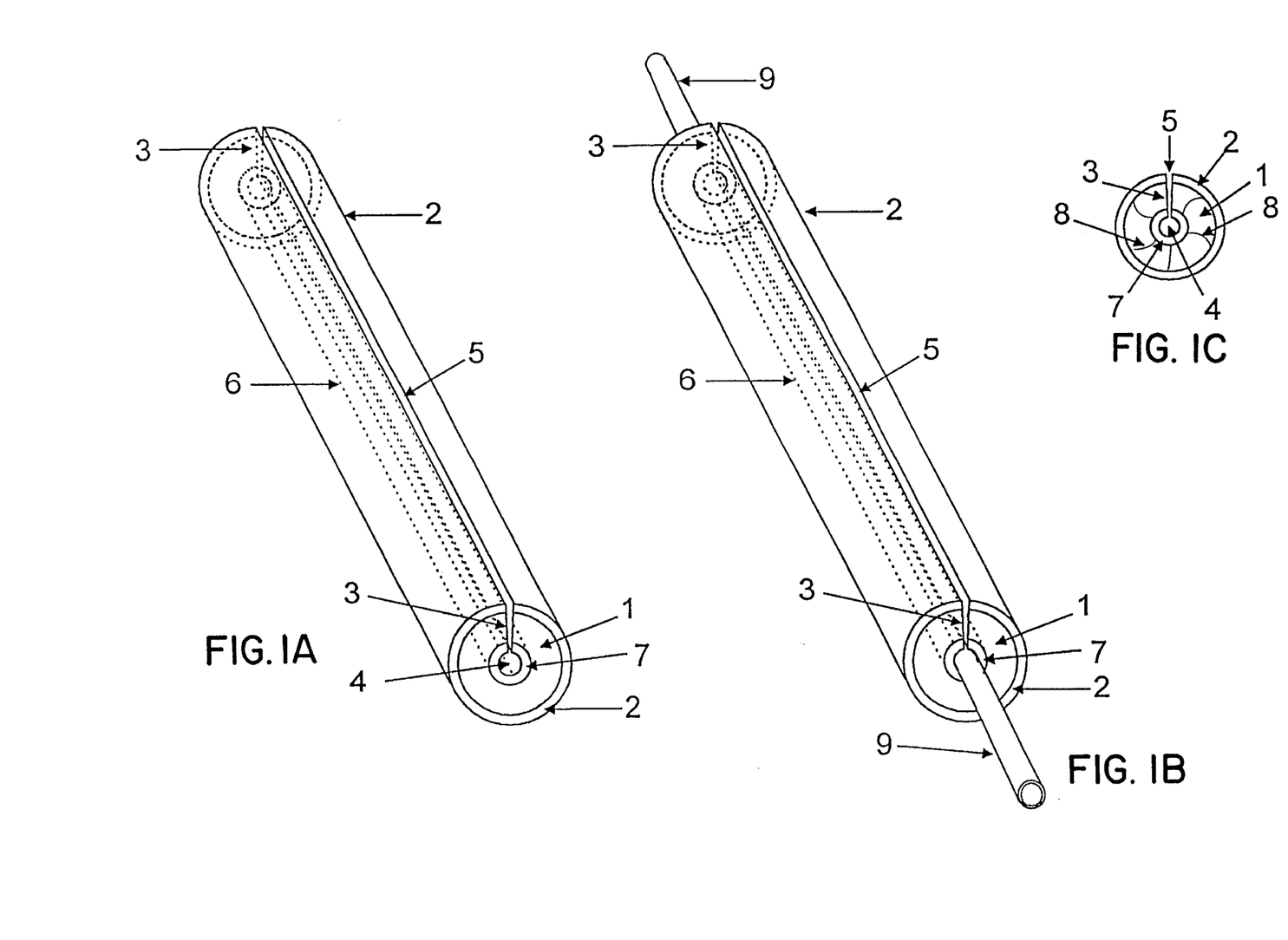
FIG. 1A is a partial cross-sectional view of a first cylindrical embodiment of the invention without I.V. tubing in place.
FIG. 1B is a partial cross-sectional view of a first cylindrical embodiment of the invention with I.V. tubing in place.
FIG. 1C is a cross-sectional view of a first cylindrical embodiment without I.V. tubing in place.

Referring now to the drawings, FIG. 1 is a view of the first embodiment of the invention I.V., administration tubing in place at 4. The insulation device or covering consists of an inner tubular channel 7 with an access split 5 at the top and attached to an outer tubular channel 2 by means of two central support structures 3. The two central support structures 3 are placed between the openings of inner and outer tubular channels 7,2 and run the length of the insulation covering. A separating, insulating space 1 is maintained between the inner tubular channel 7 and the outer tubular channel 2.

Ancillary support structures 8 as depicted in FIG. 1C may be required to maintain centering of the inner tubular channel 7 within the outer tubular channel 2 and these could run the length of the insulation covering. The number and placement of the ancillary support structures 8 can be varied about the circumferences of the inner and outer tubular channels 7,2 as shown in FIG. 1C. It may be necessary only to have one, two or three appropriately placed ancillary support structures 8 to maintain centering of the inner tubular channel 7 throughout the length of the insulation device. The support structures can be of the same plastic material as the inner and outer channels and can be formed integrally therewith.

The patient's I.V. administration tubing 9 would be inserted into the insulation covering by widening the access slit 5 at one end of the insulation device and pressing a small section of the I.V. administration tubing 9 through the access slit 5 into the inner tubular space 4, and then continuing to push the I.V. administration tubing 9 down the length of the access slit 5, widening the access slit 5 as the I.V. administration tubing 9 advances down the length of the insulation device and closes the access slit 5 above it. After insertion of the I.V. administration tubing 9, the access slit 5 can be sealed with tape or velcro closure or other closure means, not shown, to keep the I.V. administration tubing 9 secured within the insulation device.

The overall length of the insulation device can be made to provide coverage of the length of the patient's I.V. administration tubing 9 and can come as one, two or more sections. The I.V. drip chamber and flow rate controller of the I.V. administration set (not shown) can be excluded from the insulation device by attaching one sectional length of the insulation device on the tubing between the I.V. reservoir bag and the drip chamber. Further, another sectional length of the insulation device can be applied between the drip chamber and patient's anatomic I.V. site. Alternatively, the insulation device can incorporate the drip chamber by increasing the diameters (not shown) of the inner and outer tubular channels 7,2 to accommodate the short sectional length of any larger tubular drip chambers. The flow rate controller of the I.V. administration set is usually of a thumb-wheel roller clamp type that can be partially or completely placed inside the inner tubular channel 7 providing insulation while permitting access to adjust I.V. fluid flow rate.

In FIGS. 1A, 1B, 1C, the wall thickness of the inner and outer tubular channels 2,7 can be adjusted to permit various degrees of rigidity for purposes of 1) easy insertion of the I.V. administration tubing 9 and 2) flexibility of the applied insulation device during patient use to permit bending about the patient's arms or other operating room structures and thereby avoiding kinking and undue stress to the inserted I.V. tubing 9. All components can be made of transparent plastic-like material to permit visualization of the inserted I.V. administration tubing 9. This will permit the easy detection of air bubbles in the fluid of the I.V. tubing 9 when in patient use.

Representative examples of suitable plastic materials that can be used to provide a transparent insulation covering includes a variety of thermoplastic materials. Representative examples of suitable polymeric materials that can be used comprise polyethylene, polypropylene, polyurethane, polyvinyl chloride, silicone, and the like. The plastic wrap material insulating means can be manufactured by known methods including extruding and other molding processes.

Figure 2A:
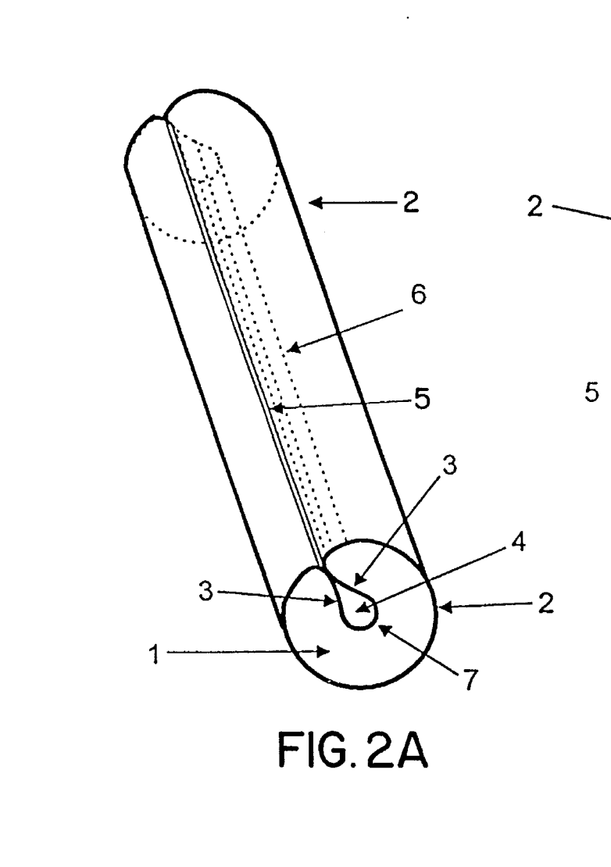
FIG. 2A is a partial cross-sectional view of a second cylindrical embodiment without I.V. tubing in place.
Figures 2B, 2C:
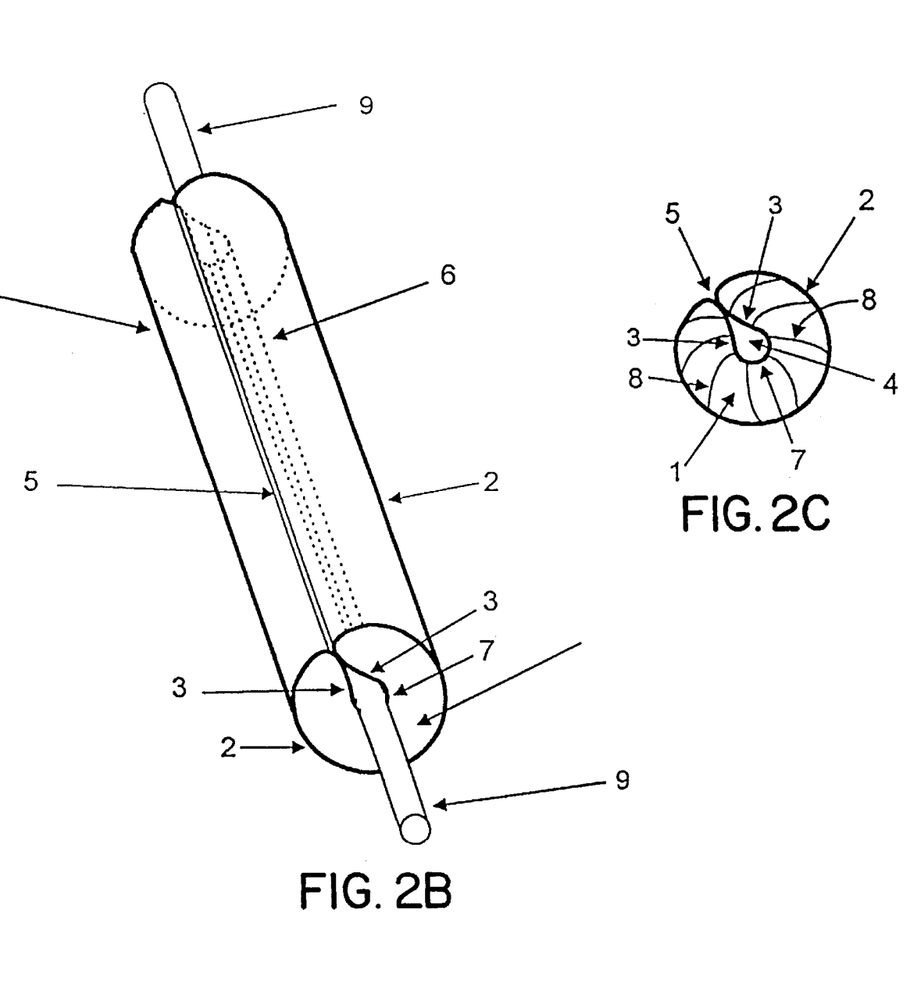
FIG. 2B is a partial cross-sectional and longitudinal view of a second cylindrical embodiment with I.V. tubing in place.
FIG. 2C is a cross-sectional view of a second cylindrical embodiment without I.V. tubing in place.

FIGS. 2A, 2B, 2C depict a second embodiment of the insulation device. An inner tubular channel 4 (in which a I.V. administration tubing is to be placed) is formed by the surfaces of 3,7 during the manufacturing process by everting or depressing a flexible tube 2 (outer covering) to permanently form the inner tube-like channel 4 which may be tear-drop shaped (as in FIG. 2A) or more circular-shaped depending upon manufacturing process. The inner tube-like channel formed by 3,7 is open at one point 5 to form an access slit 5 through which to insert the I.V. administration tubing 9 (containing the warm fluid to be insulated) into the inner tube-like space 4. An insulating space 1 separates the inner tube-like channel formed by 3,7 from the outer insulation covering 2. After the I.V., tubing 9 is inserted into the inner tube-like channel 3,7, the slot of the access slit 5 can be sealed closed with tape, not shown. The wall thickness of the inner tube-like channel (formed by the surfaces of 3,7) and the outer insulation covering 2 can be adjusted to permit various degrees of rigidity for purposes as stated for the previous embodiment. All components should ideally be made with transparent plastic-like material to permit easy visualization or detection of air bubbles within the fluid of the I.V. tubing 9 when in patient use.

Ancillary support structures 8 as depicted in FIG. 2C can be used to maintain centering of the inner tubular channel 3,7 within the outer tubular channel 2 and these can run the length of the insulation device and can be bonded thereto or integral therewith. Preferably the supports are the same plastic as the insulation covering. The number and placement of the ancillary support structures 8 can be varied about the inner tear-drop shaped channel 3,7 as shown FIG. 2C. It may be necessary only to have one, two or three appropriately placed ancillary support structures 8 to maintain centering of the inner tear-drop shaped channel 3,7 throughout the length of the insulation device.

Figures 3A, 3B, 3C, 3D, 3E:
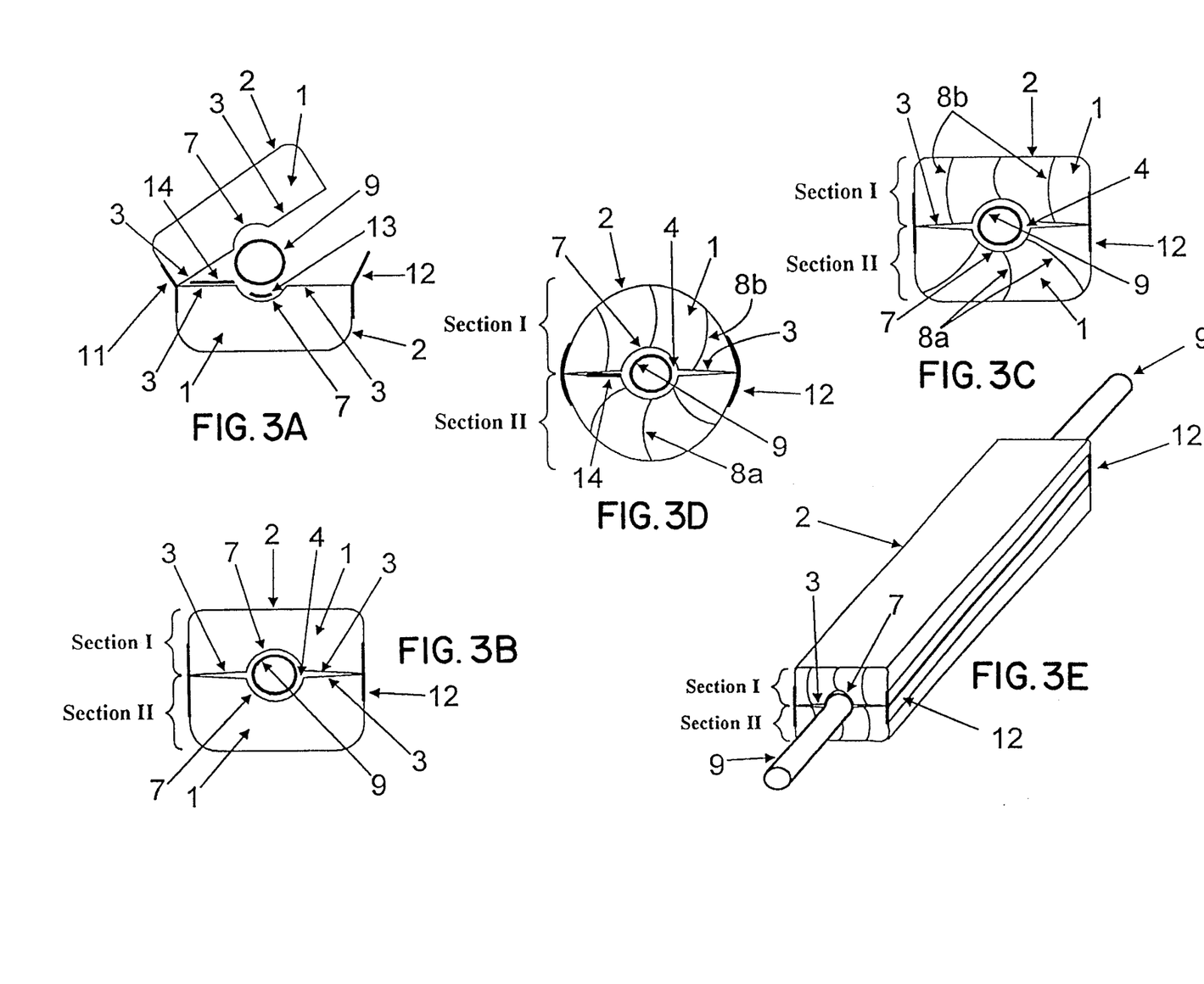
FIG. 3A is a cross-sectional view of a third embodiment, with upper and lower rectangular sections hinged and opened on one side to accept I.V. tubing.
FIG. 3B is a cross-sectional view of a third embodiment, with upper and lower rectangular sections closed around the I.V. tubing.
FIG. 3C is a cross-sectional view of a third embodiment, with upper and lower rectangular sections closed around the I.V. tubing and demonstrating ancillary center, support structures.
FIG. 3D is a cross-sectional view of a third embodiment, with upper and lower semi-cylindrical sections closed around the I.V. tubing and demonstrating ancillary center, support structures.
FIG. 3E is a partial cross-sectional and longitudinal view of a third rectangular embodiment with I.V. tubing in place.

FIGS. 3A, 3B, 3C, 3D, 3E illustrate a third embodiment of the insulation device. An inner tubular space 4 outlined by indentation 7 in all depictions of FIG. 3 is formed by the application of an upper Section I and Section II of the insulation device to enclose the I.V. tubing 9. Sections I & II are similar and intended to oppose each other as shown in all illustrations of FIG. 3. Section I of the device has two companion surfaces 3 of Section II to form a support structure 3 and a semi-tubular indentation surface 7 around which the I.V. tubing will be enclosed. The indentation surface 7 as shown in FIG. 3A may be preformed at the time of manufacture or be absent (not shown) until formed at the time of I.V. tubing 9 insertion by the user. Sections I & II of the device can be hinged with an adhesive tape-like material 11 or a hinge of the same plastic material as the covering and formed as an integral part thereof to facilitate insertion of the I.V. tubing 9 as shown in FIG. 3A.

Further, another adhesive tape-like or bonding material 14 can be applied to partially seal (in combination with adhesive tape-like material 11) Sections I & II together before insertion of the I.V. tubing 9. Further, another adhesive tape-like or bonding material 13 may be applied to secure the I.V. tubing 9 in place when it is inserted into the opposed Sections of I and II in FIG. 3A at indentation 7. Finally, an adhesive tape-like or velcro securing material 12 or similar means will be applied to seal the I.V. tubing 9 centered within Sections I & II at indentation surface 7 as depicted in FIG. 3B. An insulating space 1 will be provided within the device bounded by the surface of 2,3,7 of Sections I & II.

The combined shape of Sections I & II, as depicted in FIGS. 3A, 3B, 3C, 3E is of a rounded rectangular form, but can be of another geometric shape as shown in FIG. 3D which is of circular or cylindrical means. Other two dimensional geometric shape means could be employed such as square, hexagon, octagon, or polygon (not shown) to extrude an alternate three dimensional exterior.

Ancillary support structures 8a, 8b as shown in FIGS. 3C, 3D, 3E can be employed to maintain the I.V. tubing 9 centered within the combined Sections of I & II to insure an insulating space 1 is maintained between the outer surface 2 and inner tubular channel formed by the indentation surfaces 7 of Sections of I & II. The attachments of these ancillary support structures 8a can be from the outer surface 2 of the device to the surface of 7 as depicted in Section II of FIG. 3C, 3D. Alternatively, the attachments of the ancillary support structures 8b can be from the surface 2 to the surface of 3 as depicted in Section I of FIGS. 3C, 3D. The number and final placement of these ancillary support structures 8a, 8b can be a combination of both types 8a, 8b as described above.

Figure 4A:
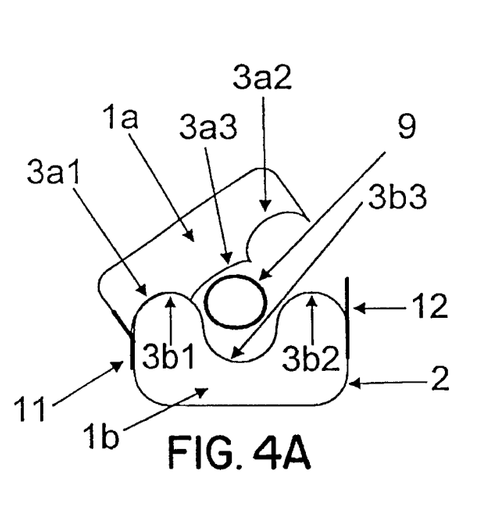
FIG. 4A is a cross-sectional view of a fourth embodiment, with upper and lower rectangular, mating sections hinged and opened on one side to accept I.V. tubing.
Figure 4B:
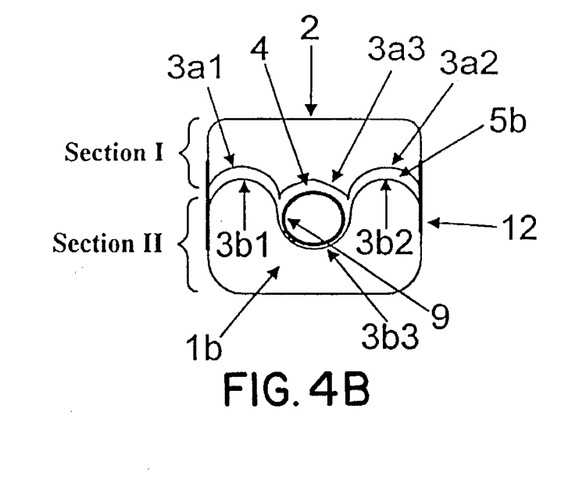
FIG. 4B is a cross-sectional view of a fourth embodiment, with upper and lower rectangular mated sections closed around the I.V. tubing.

FIGS. 4A, 4B, 4C, 4D show a fourth embodiment of the insulation device. The female surfaces 3a1, 3a2 of Section I are mated with the male surfaces 3b1, 3b2 of Section II as shown in FIGS. 4A, 4B. The mating of Section I with Section II form an inner tubular channel 4 for the I.V. tubing 9 bounded by the surfaces of 3a3 of Section I and 3b3 of Section II. Sections I & II are as shown and intended to mate as depicted in all embodiments of FIG. 4. Sections I & II of the device may be hinged with an adhesive tape-like material 11 to facilitate insertion of the I.V. tubing 9 as shown in FIG. 4A and are similar in function as described above for the third embodiment.

Figures 4C, 4D:
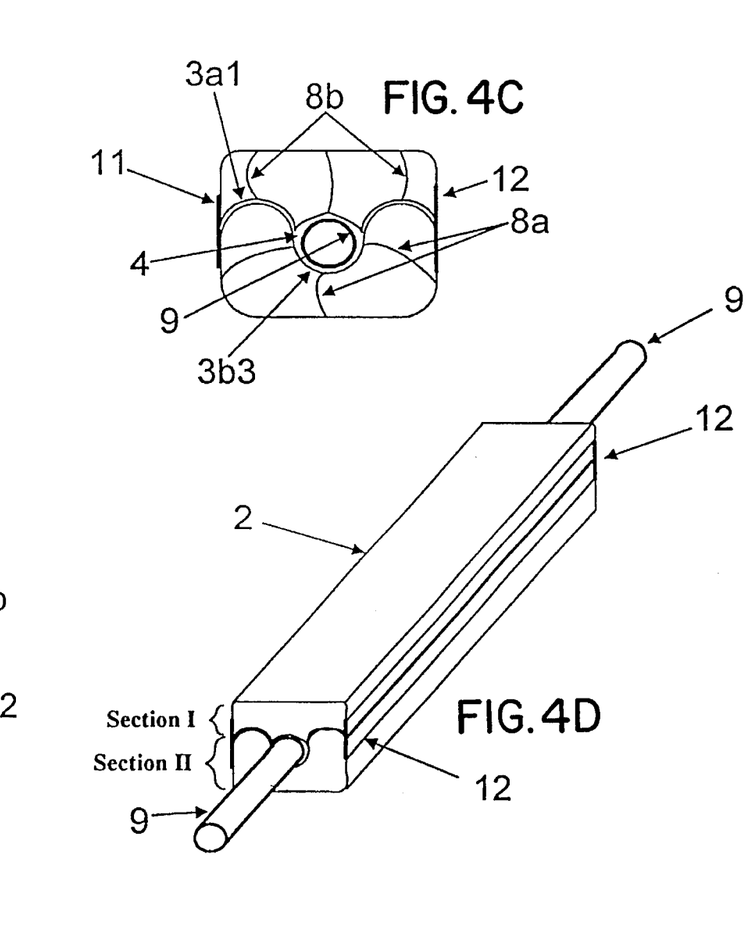
FIG. 4C is a cross-sectional view of a fourth embodiment, with upper and lower rectangular, mated sections closed around the I.V. tubing and demonstrating ancillary center, support structures.
FIG. 4D is a partial cross-sectional and longitudinal view of a rectangular, mated embodiment with I.V. tubing in place.

Ancillary support structures 8a, 8b as shown in FIGS. 4C, 4D can be employed to maintain the I.V. tubing 9 centered within the mated Sections of I and II, and are similar in construction and function as described and depicted above for the third embodiment (FIG. 3).

The shape of Sections I & II, as depicted in FIGS. 4A, 4B, 4C, 4D, are of a rounded rectangular form, but can be of another geometric shape as described above for the third embodiment (FIG. 3).

In all embodiments, the structure of the insulation device in FIGS. 1A–C, 2A–C, 3A–E and 4A–D are formed of commercially available materials and is uncomplicated and inexpensive to manufacture. It is a small, lightweight, portable and flexible covering to provide predictable insulation of I.V. administration tubing carrying warmed I.V. fluids to the patient in cooler environments. It is completely free of any attachment to a remote energy source.

In all embodiments, the internal insulation space 1, 1a, 1b can be filled with air or other clear, light-weight, insulation material to provide separation and centering of the I.V. tubing 9 within the device. The actual physical dimension of separation between the inner channel 7 and the outer channel 2 formed by embodiments one, two, and three can be varied to achieve adequate insulation and minimum bulk attached to the I.V. tubing 9. The actual physical dimension of separation between the inner channel formed by 3a3 and 3b3 and the outer channel 2 of the fourth embodiment can be varied to achieve adequate insulation and minimum bulk attached to the I.V. tubing 9.

Still further, the insulation device can be formed of a number of different sizes and lengths, so that it can accommodate larger or smaller diameter I.V. administration tube sizes and their varying lengths.

EXAMPLE

It was proposed to use external I.V. fluid warmers to pre-warm all I.V. fluids to about 40° C. and, to conserve heat energy, insulate the I.V. solution reservoir (bag or bottle) and all exposed I.V. tubing except the drip chamber and roller clamp/injection-site area during patient use.

To determine if insulating the I.V. reservoir bag and administration tubing would be an effective technique to provide warmed I.V. fluids and for how long, the following tests were performed:

I. 500 mL plastic I.V. bags of 0.9% sodium chloride solution were warmed to 40° C. and allowed to cool to an ambient temperature between 22°–23° C. Temperature curves for the decrease in temperature with time were measured about every 10 minutes within the I.V. bag with: 1) no insulation and 2) ⅝" bubble-wrap insulation, wrapped one thickness and taped in place.

II. 500 mL plastic I.V. bags were warmed to 40° C. and the fluid contents emptied through a standard I.V. administration set at 30 and 60 mL/minute flow rates. The temperature of the fluid exiting the I.V. tubing was measured every 1.5 minutes with the I.V. bag and I.V. tubing having 1) no insulation and 2) insulated with ⅝" bubble-wrap, one thickness about all surfaces taped in place, drip chamber and roller-clamp areas excluded.

The standard I.V. administration set consisted of a non-vented drip chamber, 68" of ⅛" I.V. tubing, roller clamp, injection site, 4-way stopcock, 33" of 3/16 O.D. I.V. tubing and terminated with a 16 ga 2" I.V. cannula.

Figure 5:
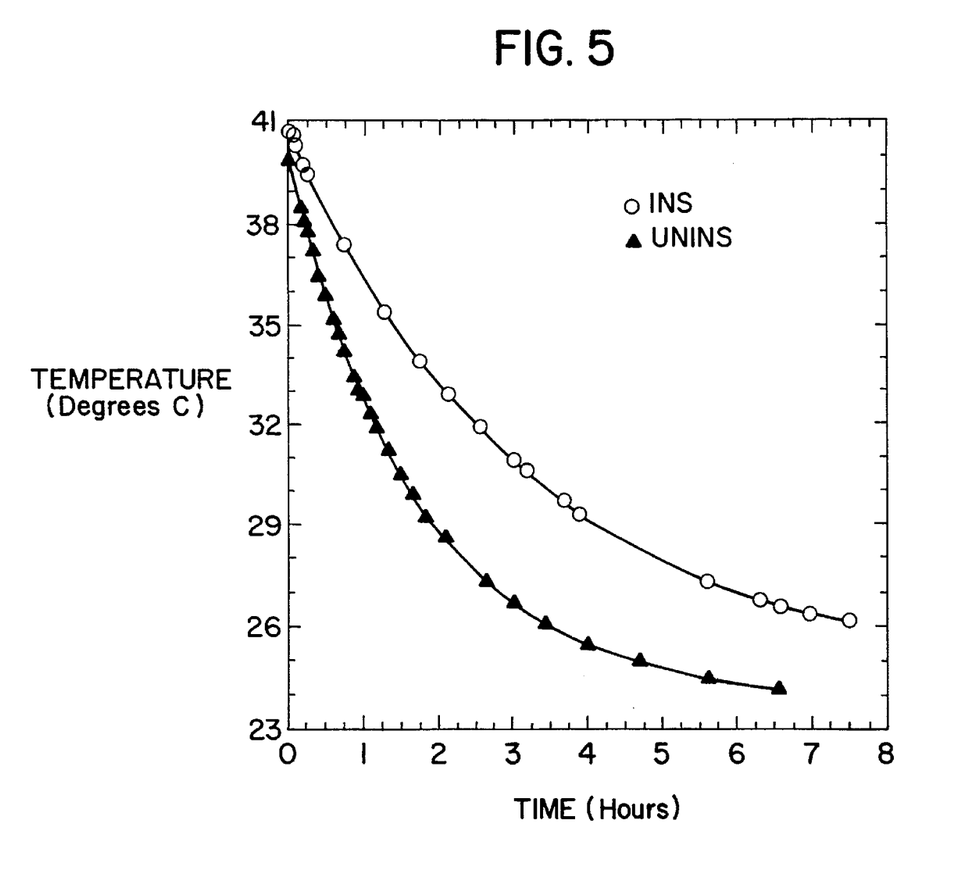
FIG. 5 illustrates the complete plot of the temperature decreases for an insulated I.V. bag and an uninsulated I.V. bag for the tests carried out in the Example.

The results of the above tests are as follows:

I.1. Warmed I.V. Bag with no insulation—temperature decreased from 40° C. to 32.8° C. at 1 hour, 28.8° C. at 2 hours, I.2. Warmed I.V. Bag with insulation—temperature decreased from 40.8° C. to 36.8° C. at 1 hour, 33.4° C. at 2 hours, FIG. 5 illustrates the complete plot of temperature decreases.

II.1. Oulet temperatures with I.V. Bag and I.V. tubing (no insulation)
  @ 30 mL/minute: temperature peaked at 35.5° C. in 2 minutes, then almost linearly decreased to 31° C. in 30 minutes.
  @ 60 mL/minute: temperature peaked at 37.2° C. in 2 minutes, then almost linearly decreased to 34.8° C. in 17 minutes.

II.2. Outlet temperatures with Insulated I.V. Bag and I.V. tubing:
  @ 30 mL/minute: temperature peaked at 37.0° C. in 2 minutes, then almost linearly decreased to 33.4° C. in 31 minutes.
  @ 60 mL/minute: temperature peaked at 38.2° C. in 2 minutes, then almost linearly decreased to 36.8° C. in 18 minutes.

Figure 6:
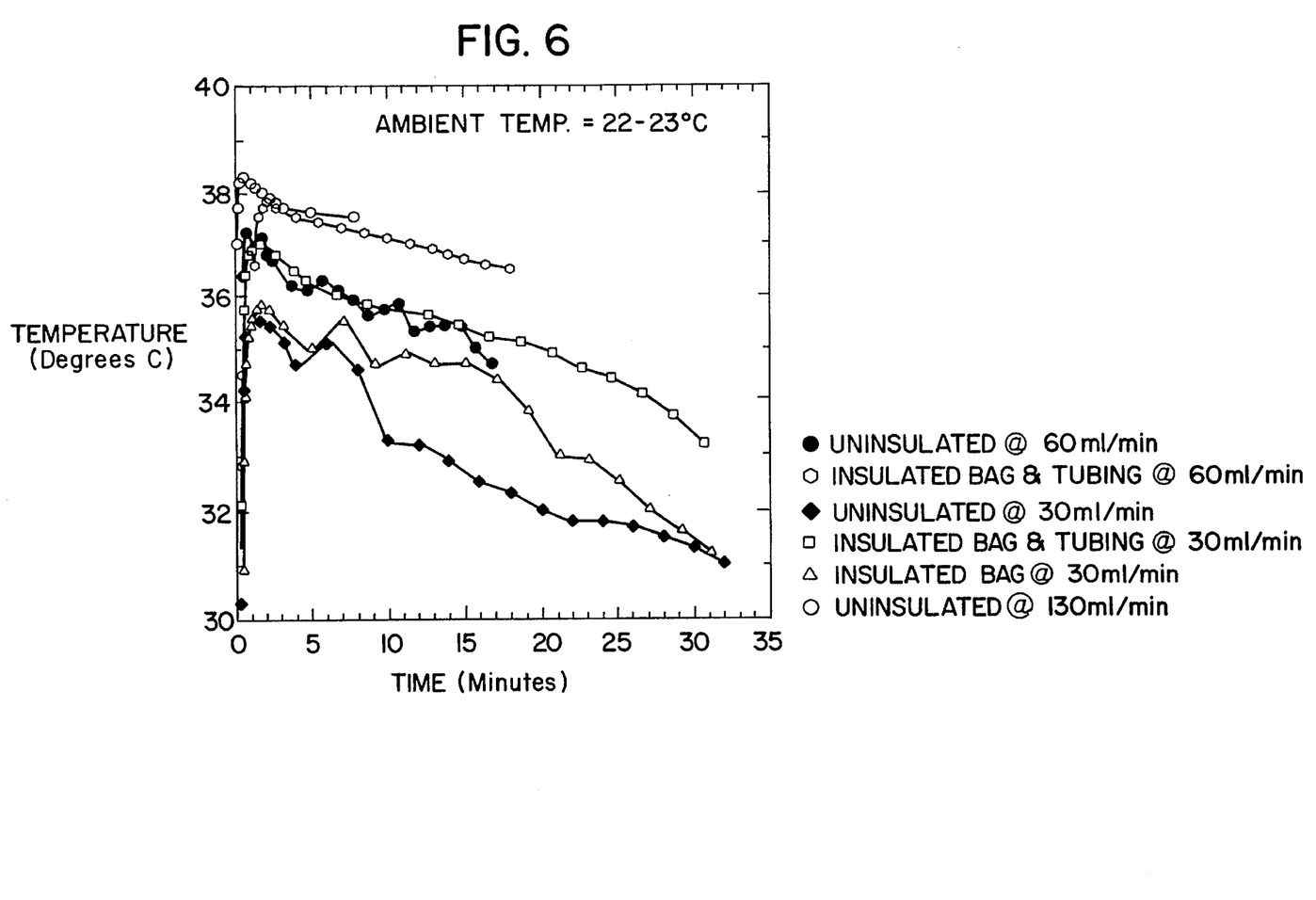
FIG. 6 illustrates the complete temperature plots at various flows for the tests carried out in the Example.

FIG. 6 illustrates the complete temperature plots.

This study demonstrates that a pre-heated I.V. fluid (to about 40° C.) container can be insulated and effectively administered through an insulated I.V. administration set at slow flow rates of 30 and 60 mL/minute, and maintain I.V. fluid temperature above 33° C. and 36° C., respectively. Faster I.V. fluid flow rates will almost certainly produce better results. In addition, the insulated pre-warmed I.V. fluid bag can remain in a warm state (above 33° C.) for about two hours. The insulation in this case was ⅝" bubble-film ("Bubble-Wrap").

While the present invention has been described in accordance with the preferred embodiments of the various figures, it is understood that other similar embodiments may be used or modifications and additions may be made to the described embodiments for performing the same functions of the present invention without deviating therefrom. Therefore, the present invention should not be limited to any single embodiment but rather construed in breadth and scope in accordance with the recitation of the appended claims.

What is claimed is:

1. An insulation device in combination with intravenous tubing, the insulation device comprising:

a flexible wrap material assembly comprising transparency to provide visibility of enclosed portions of said intraveneous tubing surrounding and insulating the intravenous tubing, said wrap material assembly including means defining an interior wall having an inner surface and an outer surface, said inner surface of said interior wall defining an interior channel; an exterior wall having an inner surface and an outer surface, said exterior wall being spaced from said interior wall so as to define an insulation air space therebetween; an access opening extending the length of the wrap material assembly from said outer surface of said exterior wall to said interior channel for insertion of the intravenous tubing; and support means comprising a plurality of spaced structures for maintaining the interior channel generally centered within the exterior wall so as to maintain said insulating air space between the interior and exterior walls.

2. The combination of claim 1 further comprising closure devices for securing the intravenous tubing within the wrap material assembly.

3. The combination of claim 1 further comprising means for accommodating at least one of drip chambers, flow rate controllers, injection sites, and like components of intravenous administration equipment.

4. The combination of claim 1 wherein the said plurality of spaced structures extend along the length of the interior and exterior walls and is positioned in the insulation air space.

5. The combination of claim 1 wherein the wrap material assembly comprises two mating portions each having a said interior wall, exterior wall, and insulation air space, the interior wall of each said mating portion being concavely curved so as to accommodate the intravenous tubing, and said mating portions being hinged together along one side thereof to facilitate insertion of the intravenous tubing.

6. The combination of claim 5 further comprising closure means at a side opposite the hinged side to secure the intravenous tubing between the mating portions.

7. The combination of claim 1 wherein the insulation air space is at least partially filled with light weight, transparent insulation material.

8. The combination of claim 1, wherein said interior wall is configured so as to be substantially continuous and to substantially correspond to the exterior configuration of said intravenous tubing disposed therewithin.

9. The combination of claim 1, wherein said wrap material assembly is substantially entirely transparent.

10. An insulation device in combination with intravenous tubing, the insulation device comprising:

a wrap assembly comprising transparency to provide visibility of enclosed portions of said intraveneous tubing encircling and insulating the intravenous tubing, the wrap assembly having an inner wall for defining an interior channel extending along the length thereof; said inner wall having inner and outer surfaces; an outer wall spaced from said inner wall by a plurality of spaced structures, said outer wall having inner and outer surfaces; an insulation air space being defined between said inner and outer walls; and a parting slit being defined along the length of said wrap assembly and between said outer surface of said outer wall and said inner surface of said inner wall thereby to define an access opening for selective insertion of the intravenous tubing into said interior channel.

11. The combination of claim 10, further comprising at least one closure device for selectively closing at least a portion of said slit thereby to retain said intravenous tubing within said wrap assembly.

12. The combination of claim 5, wherein said plurality of spaced structures comprise a plurality of spaced-apart support elements each extending between and connecting said inner and outer walls.

13. The combination of claim 10, wherein said wrap assembly comprises first and second mating wrap portions each having an inner wall element and outer wall element, said inner wall elements of said mating wrap portions together defining said interior channel.

14. The combination of claim 13, wherein said mating portions are hingedly coupled along one side edge thereof.

15. The combination of claim 14, further comprising a closure assembly for selectively securing said mating portions at a side opposite said one side.

16. The combination of claim 10, wherein said insulation space is at least partially filled with a lightweight transparent insulation material.

17. The combination of claim 10, wherein said wrap material assembly is substantially entirely transparent.

* * * * *